United States Patent
Calvert et al.

(10) Patent No.: US 10,823,795 B2
(45) Date of Patent: Nov. 3, 2020

(54) SUPPORT OF SUPERCONDUCTING COILS FOR MRI SYSTEMS

(71) Applicant: SIEMENS HEALTHCARE LIMITED, Camberley (GB)

(72) Inventors: Simon James Calvert, Chipping Norton (GB); Jonathan Noys, Abingdon (GB)

(73) Assignee: Siemens Healthcare Limited, Camberley (GB)

( * ) Notice: Subject to any disclaimer, the term of this patent is extended or adjusted under 35 U.S.C. 154(b) by 389 days.

(21) Appl. No.: 15/521,837

(22) PCT Filed: Oct. 22, 2015

(86) PCT No.: PCT/EP2015/074525
§ 371 (c)(1),
(2) Date: Apr. 25, 2017

(87) PCT Pub. No.: WO2016/066526
PCT Pub. Date: May 6, 2016

(65) Prior Publication Data
US 2017/0248667 A1    Aug. 31, 2017

(30) Foreign Application Priority Data

Oct. 27, 2014 (GB) .................................. 1419124.1
Oct. 27, 2014 (GB) .................................. 1419125.8
Sep. 4, 2015 (GB) .................................. 1515687.0

(51) Int. Cl.
*H01F 1/00* (2006.01)
*G01R 33/3815* (2006.01)
*G01R 33/38* (2006.01)
*H01F 6/06* (2006.01)
*A61B 5/055* (2006.01)
*G01R 33/385* (2006.01)
(Continued)

(52) U.S. Cl.
CPC ..... *G01R 33/3815* (2013.01); *G01R 33/3802* (2013.01); *H01F 6/06* (2013.01); *A61B 5/055* (2013.01); *G01R 33/385* (2013.01); *H01F 7/20* (2013.01); *H01F 41/048* (2013.01)

(58) Field of Classification Search
CPC ....................... G01R 33/3815; G01R 33/3802; G01R 33/48; G01R 33/385; H01F 6/06; H01F 6/04; H01F 41/048
USPC ........................................................ 335/216
See application file for complete search history.

(56) References Cited

U.S. PATENT DOCUMENTS 5,153,546 A * 10/1992 Laskaris ................ G01R 33/28
                                                            324/318
5,173,677 A   12/1992 Dederer et al.
5,227,755 A    7/1993 Westphal et al.
(Continued)

FOREIGN PATENT DOCUMENTS

CN    101075497 A    11/2007
CN    103620436 A     3/2014
(Continued)

*Primary Examiner* — Shawki S Ismail
*Assistant Examiner* — Lisa N Homza
(74) *Attorney, Agent, or Firm* — Schiff Hardin LLP

(57) ABSTRACT

A resin-impregnated superconducting coil has axially-extending coil mounting arrangements that include features embedded within the structure of the resin-impregnated superconducting coil, between layers of turns of the coil.

25 Claims, 12 Drawing Sheets

(51) Int. Cl.
*H01F 7/20* (2006.01)
*H01F 41/04* (2006.01)

(56) References Cited

U.S. PATENT DOCUMENTS

| | | | |
|---|---|---|---|
| 5,237,300 A | | 8/1993 | Ige et al. |
| 5,325,080 A | * | 6/1994 | Chandratilleke ......... H01F 6/00 335/216 |
| 7,053,740 B1 | | 5/2006 | Laskaris |
| 2007/0257754 A1 | * | 11/2007 | Gilgrass ............. G01R 33/3802 335/216 |
| 2011/0015078 A1 | * | 1/2011 | Gao ................... G01R 33/3403 505/162 |
| 2011/0193665 A1 | | 8/2011 | Huang et al. |
| 2014/0171329 A1 | * | 6/2014 | Tsuda ................... G01R 33/288 505/162 |
| 2014/0274721 A1 | * | 9/2014 | Calvert ............. G01R 33/3854 505/162 |
| 2014/0274722 A1 | * | 9/2014 | Calvert ............. G01R 33/3815 505/163 |

FOREIGN PATENT DOCUMENTS

| | | |
|---|---|---|
| CN | 104038028 A | 9/2014 |
| DE | 68907278 T2 | 2/1994 |
| DE | 102011077457 A1 | 12/2012 |
| EP | 2 075 805 A1 | 7/2009 |
| GB | 2 294 592 A | 5/1996 |
| GB | 2299672 A | 10/1996 |
| GB | 2 432 725 A | 5/2007 |
| GB | 2 432 898 A | 6/2007 |
| GB | 2437114 A | 10/2007 |
| GB | 2480636 A | 11/2011 |
| GB | 2489126 A | 9/2012 |
| GB | 2503190 A | 12/2013 |
| GB | 2519811 A | 5/2015 |
| GB | 2528947 A | 2/2016 |
| GB | 2532314 A | 5/2016 |
| JP | S56137605 A | 10/1981 |
| JP | S62287605 A | 12/1987 |
| JP | S63271907 A | 11/1988 |
| JP | H0378213 A | 4/1991 |
| JP | 2008000324 A | 1/2008 |

* cited by examiner

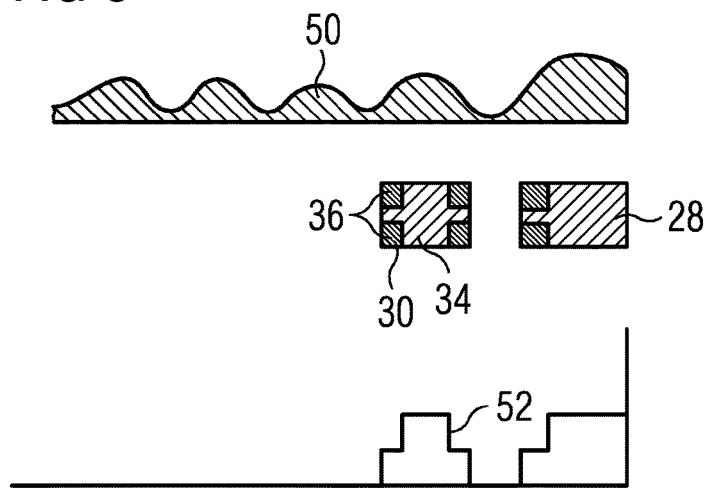
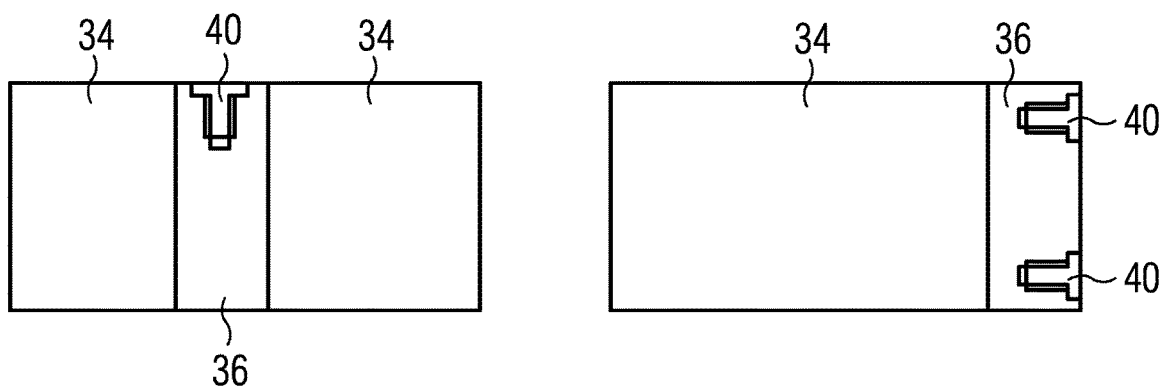
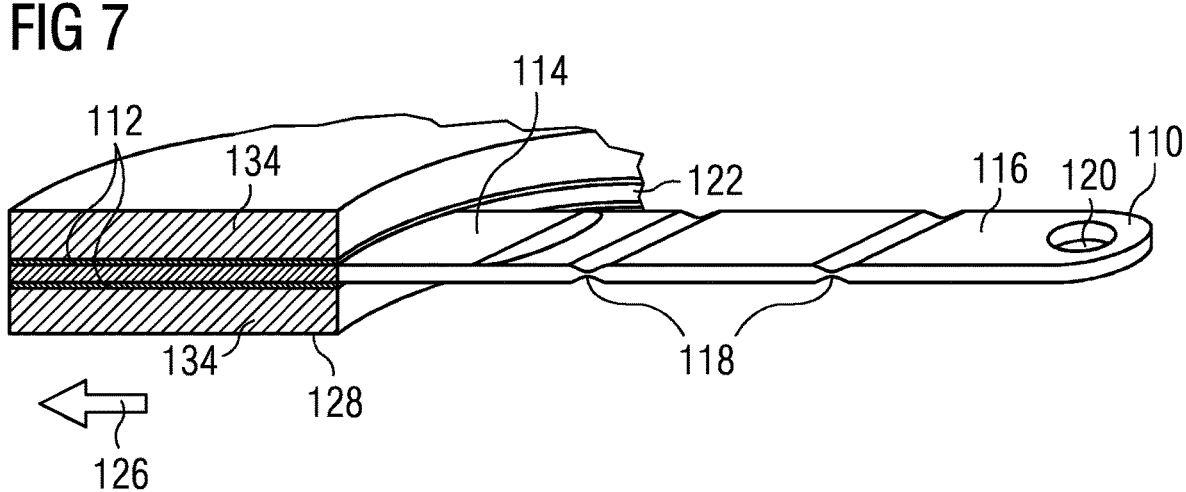

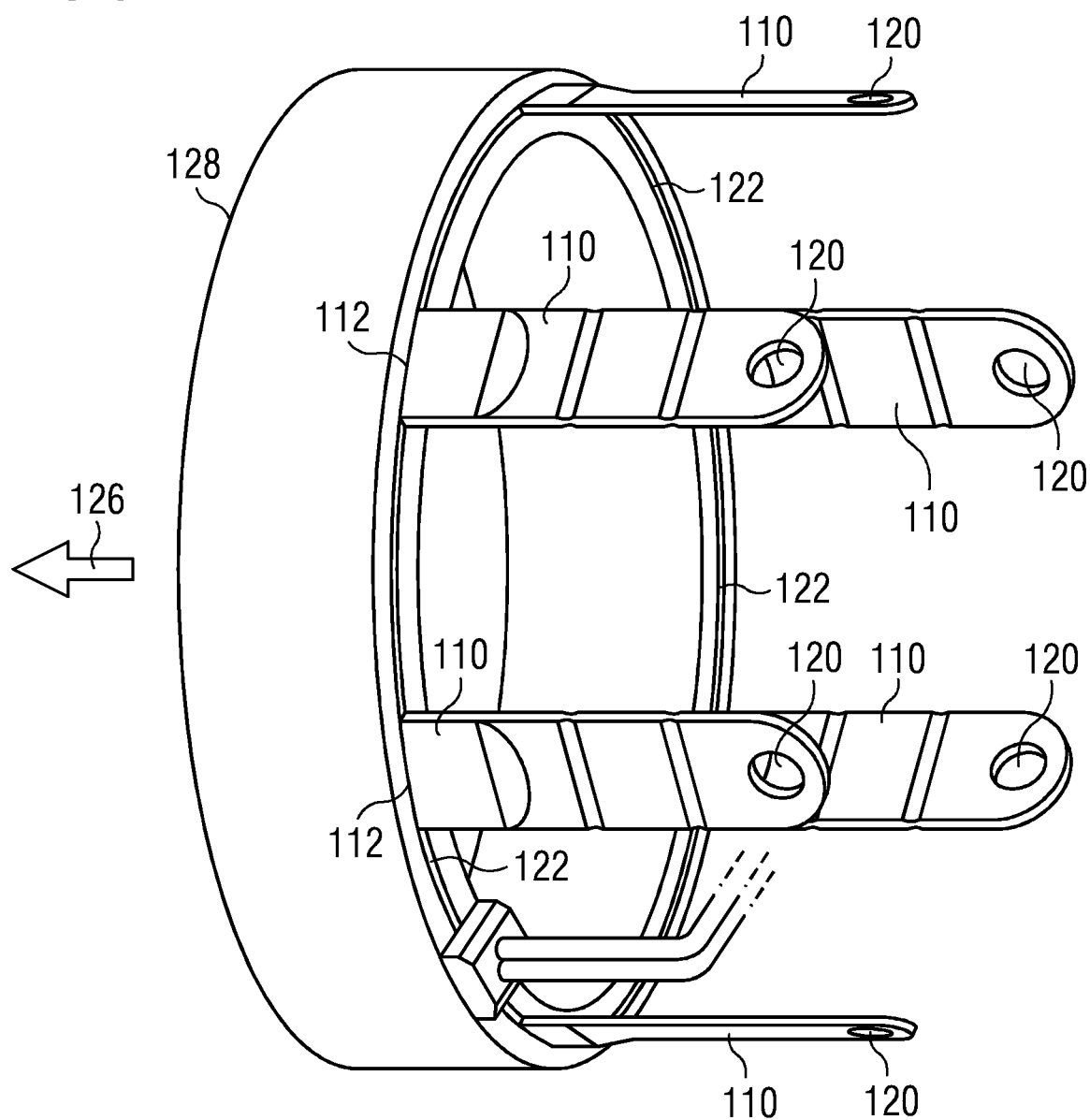

US 10,823,795 B2

SUPPORT OF SUPERCONDUCTING COILS FOR MRI SYSTEMS

BACKGROUND OF THE INVENTION

Field of the Invention

The present invention provides arrangements for supporting superconducting coils in a cost-efficient manner while minimizing undesirable interactions between the coils and the supporting structure which are known to be a major cause of undesirable spontaneous quenching. A quench is an event when the superconducting coils rapidly revert to their non-superconducting state resulting in dissipation of the energy stored in the magnet and consequent heating of the structure.

Description of the Prior Art

FIG. 1 schematically represents a radial cross-section through a conventional actively-shielded superconducting magnet for an MRI (Magnetic Resonance Imaging) system. The magnet is essentially rotationally symmetrical about axis A-A. In the present document, the term "axial" will be used to describe directions parallel to the axis A-A, while the term "radial" will be used to describe directions perpendicular to the axis A-A, extending in a plane that passes through that axis.

A magnet coil assembly 10 is mounted within a cryogen vessel 12. The cryogen vessel 12 is mounted and contained within an outer vacuum container (OVC) 14. A thermal radiation shield 16 is provided between the OVC and the cryogen vessel 12.

Magnet coil assembly 10 itself comprises inner magnet assembly 20 and shield coil assembly 22. Shield coil assembly 22 itself comprises shield coils 24 and a shield coil mounting structure 26. Inner magnet assembly 20 comprises end coils 28 and inner coils 30 connected by an inner coil mounting structure 32.

In use, end coils 28, inner coils 30 and shield coils 24 are provided with electrical current to generate a strong, homogeneous field in imaging region 21.

SUMMARY OF THE INVENTION

The present invention particularly concerns shield coil mounting structure 26 and inner coil mounting structure 32.

Cost pressures on current and future MRI systems mean that new designs require reduced material and labor contributions to enable the final system cost to be kept within acceptable limits. Conventional coil support structures consume large quantities of stainless steel, aluminum or composite materials such as glassfiber-reinforced plastic (GRP) to support the various superconducting coils, for example in cylindrical formers. Such structures may be found prohibitively expensive to produce and install on future systems.

The present invention takes advantage of the inherent strength of resin-impregnated coils. The resin-impregnated coils themselves are used as part of a mechanically self-supporting structure rather than relying on support provided by a machined former of stainless steel or aluminum, for example.

The present invention also provides a superconducting magnet structure in which the superconducting coils have a large proportion of their surfaces free and exposed to wetting by liquid, superfluid and/or gaseous cryogenic fluid.

In preferred embodiments, the superconducting magnet structure is also demountable such that materials may easily be recovered from scrap systems, and that individual coils may be removed and replaced, if required, during the service life of the superconducting magnet. It is also desirable to allow adjustment of at least some of the coils so that the required magnetic field uniformity can be achieved during manufacture.

BRIEF DESCRIPTION OF THE DRAWINGS

FIG. 5 illustrates an optimum current density distribution in an axial direction along a superconducting magnet and illustrates how an embodiment of the present invention may be used to contribute to achieving a current density distribution approaching the optimum current density distribution.

FIG. 6 schematically illustrates a cross-section of a coil of an embodiment of the present invention.

FIG. 7 shows a schematic cross-section through a shield coil according to another embodiment of the present invention.

FIG. 8A shows a perspective view of an embodiment of the present invention as represented in FIG. 7.

DESCRIPTION OF THE PREFERRED EMBODIMENTS

Figure 2:
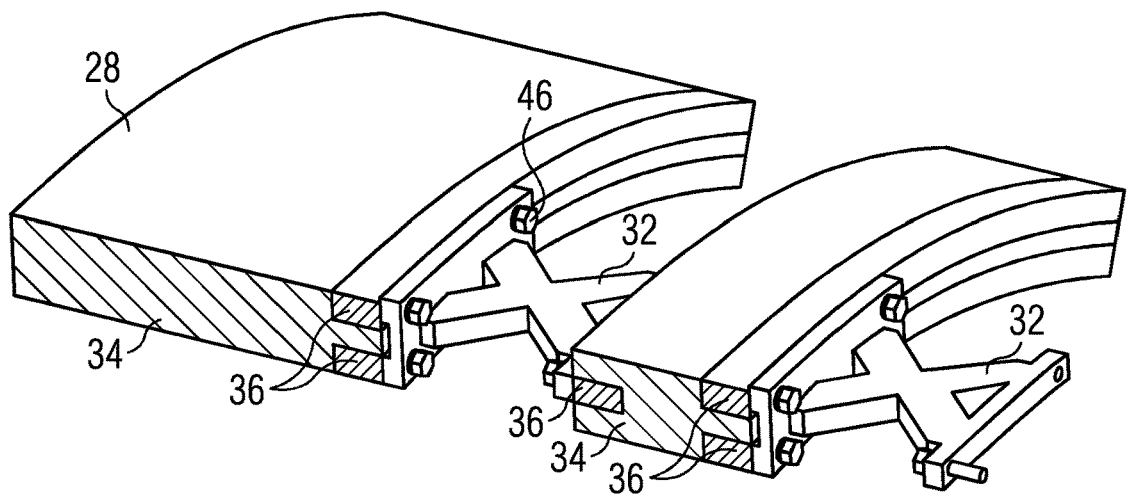
FIG. 2 shows detail of a superconducting magnet constructed according to an embodiment of the present invention.

FIG. 2 shows a detail of an embodiment of the present invention, comprising a resin-impregnated end coil 28, a resin impregnated inner coil 30 and support elements 32 mounted between the coils and joining them together.

The present invention employs impregnated coil structures which include non-coil regions, which are subsequently machined to enable assembly of the magnet.

In the case of each coil, a rectangular cross-section of impregnated material comprises regions of coil windings 34 and non-coil regions 36. The regions of coil windings 34 are made up of multiple turns of superconducting wire while the non-coil regions 36 are made up of a non-conducting filler material, such as glassfiber cloth, the whole being resin impregnated together into a single, monolithic, structure. This may be achieved by winding superconducting wire and non-conducting filler material together in the appropriate order and quantity into a mold, impregnating the resulting structure with a thermosetting resin, allowing or causing the resin to harden and removing the resulting monolithic resin impregnated structure from the mold, in a process common for the manufacture of superconducting coils and which will accordingly be familiar to those skilled in the art.

Superconducting wire is wound onto and between volumes of porous filler material to produce a volume 34 of coil turns which has a non-rectangular cross-section. In selected locations, further glassfiber cloth, or glassfiber blocks, or other porous material may be added to provide fixing points. The porous material can be added as preformed volumes. Alternatively, a tape or cord could be wound onto the tool.

The number of non-coil regions 36 per coil can be modified as appropriate to suit constraints such as required load bearing and available size.

As shown in the illustrated embodiment, each coil 28, 30 may be supported at each of its axial ends and the support elements 32 need not extend radially beyond the radial extent of the coils.

Figure 3:
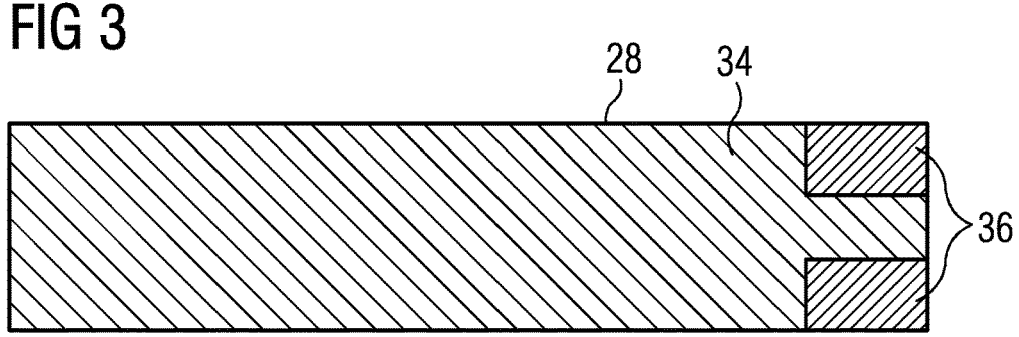
FIG. 3 shows a cross-section of an end-coil as illustrated in FIG. 2 at a certain stage in manufacture.

FIG. 3 shows a cross-section of the end coil 28, showing the regions of coil windings 34 and the non-coil regions 36. As the coil windings and non-coil regions 36 are impregnated in a single step, there are no bonded interfaces as such: a single resin body encloses the coil windings and the non-conducting filler material of the non-coil regions 36.

Figure 4:
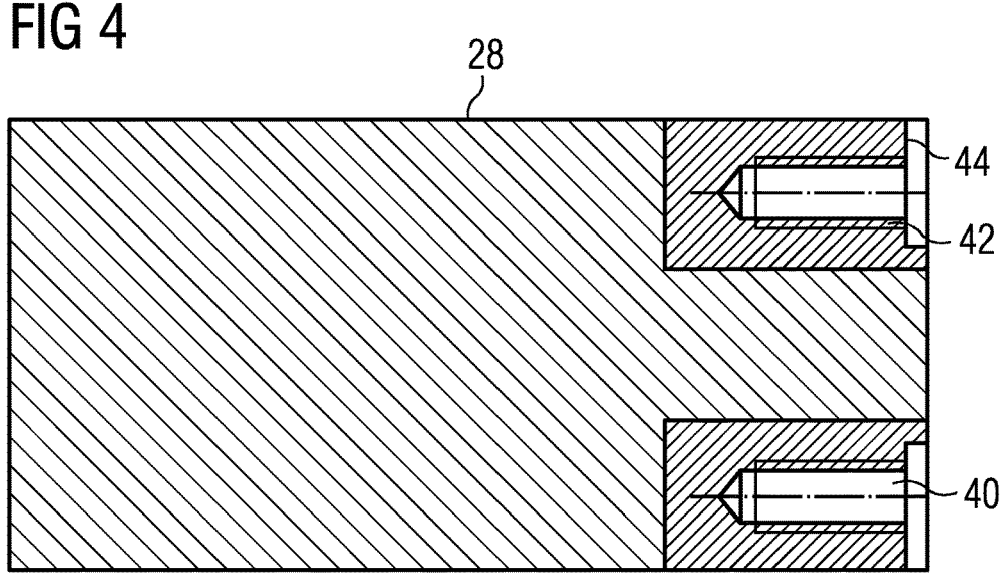
FIG. 4 shows a cross-section of an end-coil as illustrated in FIG. 2 at a later stage in manufacture.

FIG. 4 shows a cross-section of the end coil 28 of FIG. 3 in a later stage of the manufacturing process. Holes 40 are drilled in the axial end-surface of the end coil, axially into the non-coil regions 36. Preferably, these holes are tapped 42 and the adjacent axial end face may be machined flat 44 if required. The resultant holes 40 provide a mounting structure for support elements 32. As shown in FIG. 2, the support elements 32 may be fastened to the holes 40 in the non-coil regions 36 by use of screws or bolts 46 or other mechanical fastener.

Inner coil 30 is constructed in a similar manner, but in the case of inner coils, non-coil regions 36 are preferably provided on both axial surfaces, such that support elements 32 may be affixed to both axial end surfaces of the inner coil. Correspondingly, non-coil regions 36 are located at each axial end of the inner coil 30 to provide mounting structures for the support elements 32, for example in the form of tapped holes such as illustrated in FIG. 4, to receive screws or bolts 46 or similar mechanical fasteners.

Depending on the dimensional accuracy of the impregnated coil 30, and the molding technique used, it may be necessary to machine the face of the coil axial end-surface area around each hole 40 to achieve correct positioning of the coils and a final magnet with acceptable homogeneity. Such machining is preferably performed before forming the tapped holes 42, but could be performed afterwards.

Figure 20:
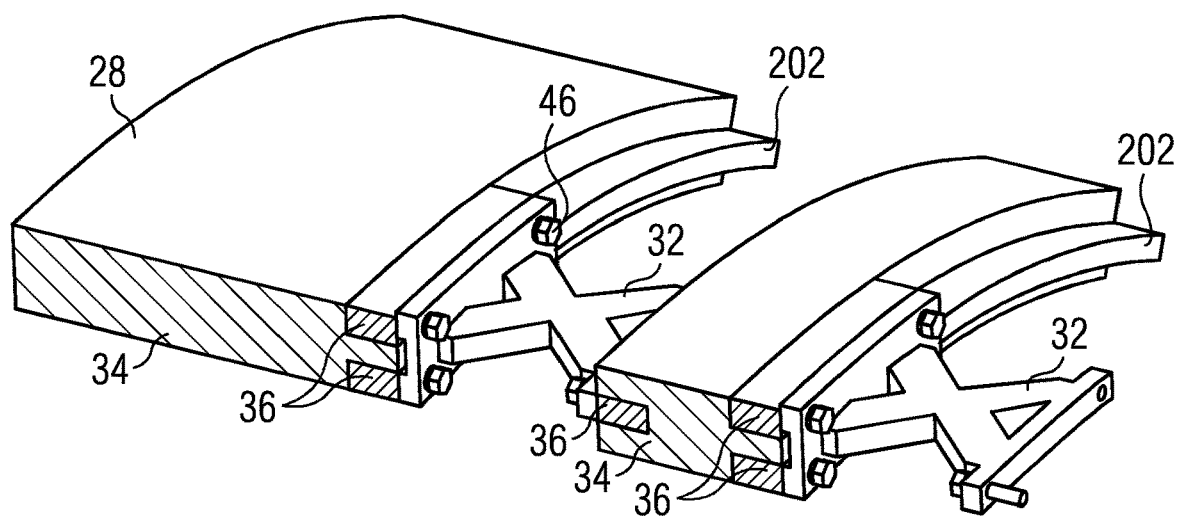
FIG. 20 shows a variant of the embodiment of FIG. 2.

As illustrated in FIG. 2, the axial end surfaces of a coil may be provided with a single annular non-coil region 36, or two or more annular non-coil regions 36. Other embodiments are of course possible. For example, as illustrated in FIG. 20, intermittent regions 202 of non-coil volume may be provided to reduce material consumption as opposed to continuous regions of non-coil volume. An appropriate tooling solution may be devised by those skilled in the art to provide the ability to manufacture this component.

The support elements 32 must be accurately dimensioned in the axial direction to ensure accurate spacing of the coils, but the other dimensions of the support elements 32 are not critical. This means that the spacer elements may be produced by any of a large number of manufacturers globally by an inexpensive process such as casting of aluminum or a composite material, injection molding or machining from a block of material, or in some embodiments by cutting from a sheet of material, depending on the load they must support. Careful selection of the materials used may provide significant benefits, allowing control of differential thermal contraction between components. This may be a significant issue when cooling the magnet down from ambient temperature at about 300K to the magnet operating temperature of about 4.2K.

Once the spacers have been produced by the inexpensive method, a single machining step may be applied to achieve the correct axial dimension. Axial end-surfaces of the support elements may then be mounted in contact with the axial end-surfaces of the coils, onto the machined faces 44 where provided.

The supporting elements 32 can be optimized to give high axial compressive strength and relatively low radial stiffness to provide radial flexure to accommodate adjacent coils at different temperatures and hoop loads, which mean that the physical size of the coil would vary over time.

The structure illustrated in FIG. 2 may be repeated so that all inner coils 30 and end coils 28 are attached together by support elements 32 of the present invention. The resultant assembly may be mounted within cryogen vessel 12 by any appropriate conventional means.

Shield coils 24 may also be constructed with a cross-section similar to that shown in FIGS. 3, 4 and mounted to support structure 26 by a similar arrangement of fasteners 46. A number of support elements 32 may be provided around each shield coil, to attach the shield coil to support structure 26; alternatively, the support structure 26 may be suitably shaped and dimensioned to interface directly with the shield coils 24 using suitable fasteners and non-coil volumes 36 as discussed above. The support structure 26 for the shield coils may be mounted on support elements 32 of the inner magnet assembly 20.

According to the present invention, material usage in the manufacture of the superconducting magnet coil structure 10 is reduced as compared to conventional arrangements using formers and the like, due to the position of the support elements 32 directly between the coils 28, 30. The arrangement of the present invention will also minimize the bending stress on the support elements 32.

The mechanical interaction between the coils 28, 30 and the support structure 32 is simplified in the structure of the present invention, meaning that the performance of this kind of magnet should be more consistent and repeatable in terms of quench rate than conventional magnet structures using formers and the like, as the variation in contact force and area between coil and support structure is reduced.

Interface forces between the regions of coil windings 34 and support elements 32 are applied through the non-coil regions 36, being regions of composite material comprising a non-conductive filler material in a resin impregnation. This provides a more even and distributed stress at the boundary of the coil windings than a direct mechanical interface between a coil and a support structure such as a former.

As the present invention provides coil structures 28, 30 comprising coil volumes 34 and non-coil volumes 36, the axial current distribution of coils such as the illustrated end coil 28 and the illustrated inner coil 30 is not constant. This may be advantageously employed to more efficiently distribute the coil windings for the magnet, as described below with reference to FIG. 5.

Figure 1:
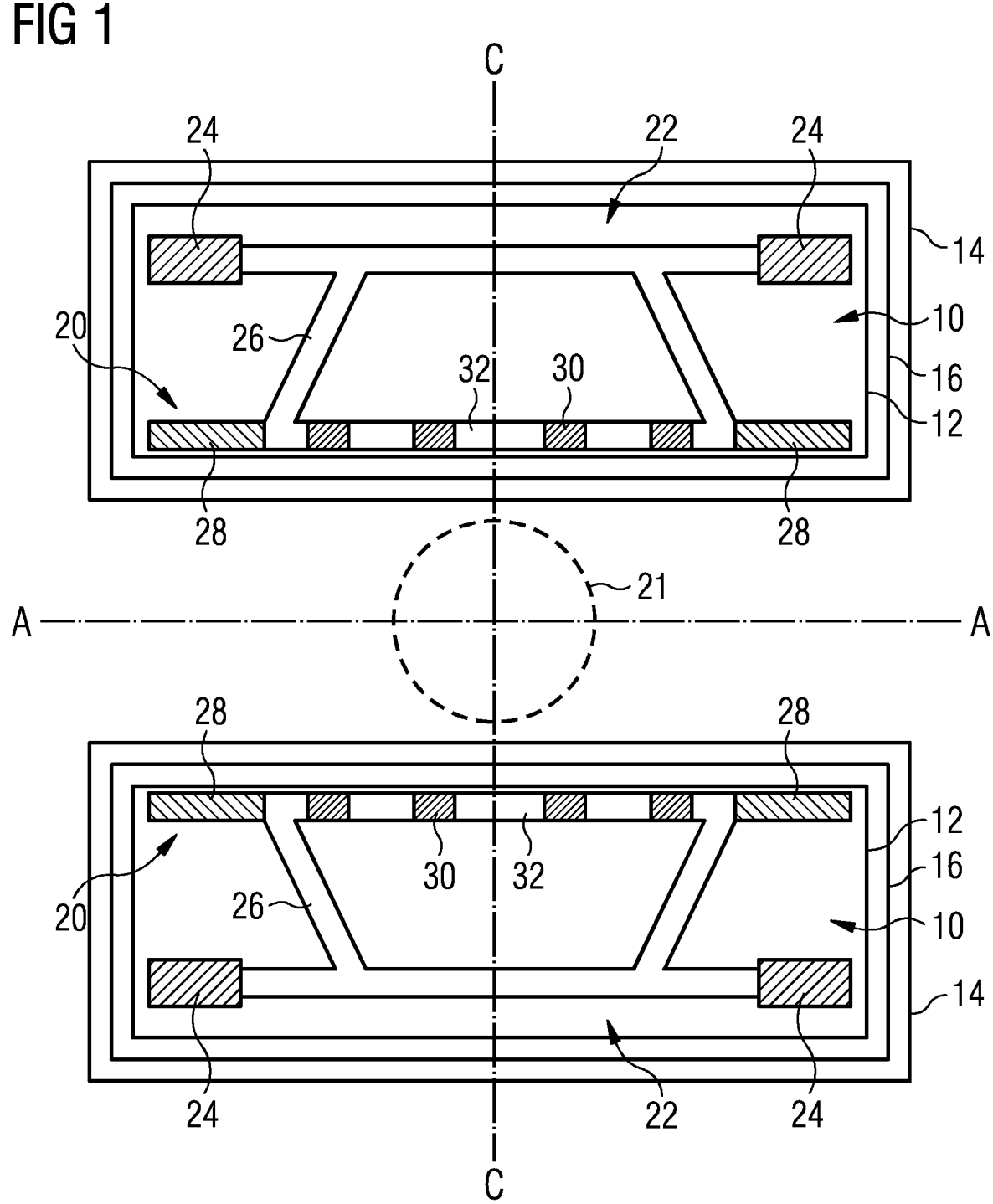
FIG. 1 shows a schematic radial cross-section of a conventional actively-shielded superconducting magnet for an MRI system.

It is known and conventional that, for a fixed inner coil diameter and current density, the optimum current distribution for field strength and homogeneity in the imaging region 21 (FIG. 1) will vary along the length of the system to give the required magnetic field homogeneity. Curve 50 in FIG. 5 shows an example optimized current density.

It is not practical to wind or provide coils distributed to match the optimized current density illustrated at 50. However, as illustrated in FIG. 5, coils 28, 30 according to the present invention have axially-outer non-coil regions 36 which have the effect of reducing the current density at the corresponding axial locations. Curve 52 illustrates the resultant axial current density when current is applied to coils 28, 30. While not matching the optimized current density of curve 50, the resultant axial current density provides a closer approximation than would be possible with magnet coils 28, 30 of rectangular cross-section.

While the assembly illustrated in FIG. 2 represents an inner magnet structure 20 of a cylindrical superconducting magnet 10, the method and structure of the present invention may be applied to active shield coils 24 which are conventionally used in cylindrical superconducting magnets for MRI systems. In such a magnet, the electrical characteristics of the magnet may determine that the support elements 32 retaining the active shield coils 24 are in tension while support elements 32 in the inner magnet structure are in compression.

By modifying the support element design, for example to enable the support element to extend in a radial direction, the present invention may be applied to retain connecting elements to support the shield coil structure 22, and support the magnet 10 by joining the magnet 10 with a cryogen vessel 12, or another part of the system if a cryogen vessel is not provided.

Figure 21:
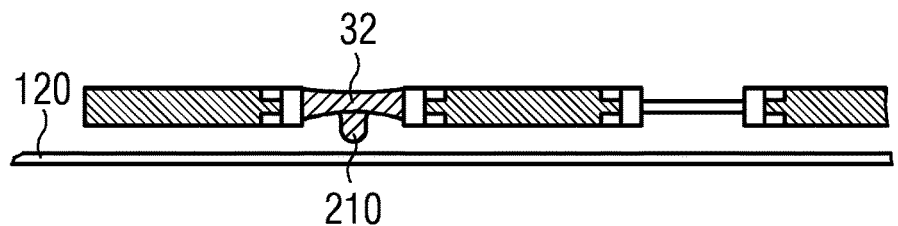
FIG. 21 shows an embodiment of the invention in which support elements bear upon a bore tube of a cryogen vessel.

FIG. 21 shows an example embodiment in which support elements 32 are provided with protrusions 210. Those protrusions bear upon a bore tube 120 of cryogen vessel 12. The protrusions 210 should be distributed around the circumference of the bore tube, providing radial support to the coil structure. Support elements 32 may also incorporate features to enable the magnet to be secured within the cryogen vessel. Protrusions 210 may be manufactured as separate components, attached to support elements 32 to provide an interface with the cryogen vessel bore tube 120.

Figure 22:
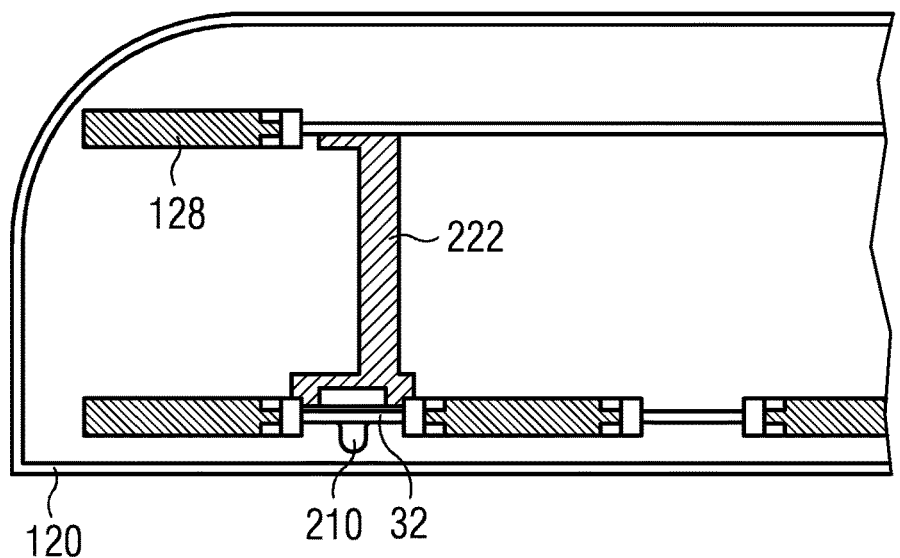
FIG. 22 illustrates an embodiment of the invention where radially-directed support members are provided.

FIG. 22 shows a further development of this principle, where radially-directed support members 222 are provided, mounted on, or bearing on, support elements 32 and retaining shield coils 128 in a required position with respect to the cryogen vessel bore tube 120. Analysis techniques, known in themselves, may be used to calculate the required load-bearing ability of the radially-directed support members 222 in use, to ensure that the required load may be safely borne by support elements 32, protrusions 120 and cryogen vessel bore tube 120.

The support elements employed in structures of the present invention are relatively small components which can be globally sourced relatively cheaply and with ease compared with existing coil support structures.

In alternative embodiments, illustrated as coil cross-sections in FIG. 6, the non-coil regions 36 may extend radially though a coil, which would reduce the complexity of winding the coil. However, the result would be to provide a coil 28 with one or two coil volumes 34 of rectangular cross section which may not be as efficient in terms of space as coil volumes 34 of non-rectangular cross section as described above. There is also not the opportunity to modulate the axial current distribution in the manner described with reference to FIG. 5.

The present invention provides a method and structure for directly supporting resin-impregnated superconducting coils by integrally formed composite non-coil regions within the coil structure. These regions are used to interface with supporting elements 32 which are used to mechanically join coils together.

Certain embodiments of the present invention may provide one or more of the following advantages.

The material and labor requirements for the support structure are minimized and therefore material usage and cost are reduced.

The method of production of the support elements (32) is simple such that they may be produced inexpensively at any of a large number of global manufacturers.\

The coil windings do not directly interact with the support elements, meaning a reduced risk of mechanical disturbances which could cause a coil to quench.

The manufacturing process may be simplified by use of a number of standard components such as the support elements 32, across a number of products. Support elements 32 may be designed and dimensioned such that they may be machined to any one of several axial lengths, enabling support elements 32 of a variety of axial lengths to be provided without the need to manufacture and stock a number of different sizes of support elements 32.

Bonding of dissimilar materials to the coils is avoided. The coil volumes 34 themselves are already composite materials, including at least a thermosetting resin and metal wires. The coil volume often also includes a filler material such as glassfiber or glass beads. By fastening the support elements 32 to the coils, the use of bonded joints to the coils is eliminated, or at least reduced. Bonded joints require cleanliness, surface preparation, and thin, even application of adhesive to avoid delamination. These requirements have been found difficult to achieve repeatedly in a production environment. The method and arrangement of the present invention has mechanically fastened joints instead, which do not have such onerous requirements.

During a quench, respective coils will heat up at differing rates. The arrangement of the present invention uses mechanically fastened joints between each coil and the corresponding coil support structure. Such mechanically fastened joints can accommodate differences in thermal expansion between coils, and between coils and a support structure without degradation. By using multiple separate support elements 32 around the circumference of the coil, the associated coils may expand and contract thermally without introducing any circumferential strain in the support elements.

Should a coil need to be changed, the mechanical joint retaining each support element 32 onto the coil can simply be disassembled, and the affected coil removed and replaced. This means a relatively low rework cost if a coil requires replacing.

The coil assembly technique of the present invention enables coil design for an effective axial current distribution profile. The coil shape promoted by the present invention provides improved wire efficiency for a given current density.

The arrangement of the present invention does not require complex tooling, as it may be produced using conventional coil winding and impregnation methods followed by simple mechanical machining steps.

The magnet structure provided by the present invention is simple, and easy to assemble.

Different designs of magnet can be produced from a limited number of "standard" coil sizes and support element sizes. Coil manufacture becomes simpler to manage, as molded coils will be produced in a limited number of "standard" sizes.

The support structure 32 is not present during the impregnation step, and so resin ingress into the support structure is not a risk, and the components of the support structure may safely be of complex shape if required. Suspension points and other features may be included which may be difficult or impossible to achieve in conventional arrangements and methods where undesirable resin ingress is an issue.

A coil support structure of the present invention may comprise a limited number of lightweight cast support elements between coils, probably a minimum of 3 support elements per coil, dependent on the expected Lorentz force between the coils. Each cast support element may weigh less than 10 kg.

It is possible to perform shimming of the resultant magnetic field by adjusting relative locations of the coils.

Once the magnet coil structure 10, comprising end coils 28, inner coils 30 and shield coils 24 is assembled, a relatively small electrical current, such as 1A, may be passed through the coils and the resultant magnetic field then measured for homogeneity. Calculations, conventional in themselves, may then be performed to determine adjustments suitable to improve the homogeneity of the measured magnetic field. At each of the fastened joints between coil and support structure 32, mechanical shims can be used to alter the coil separation and so perform the calculated adjustments. If a more dynamic solution is required then each of the coil supports could be designed to be adjustable without separating the fastened joints, for example by providing turnbuckle-style adjustment within the structure of the support elements.

Some non-coil regions may be utilized for fixing termination means or other ancillary components to, by a similar arrangement of holes and mechanical fastenings such as screws or bolts.

A further set of embodiments are illustrated in FIGS. 7-19. In these embodiments, rather than a non-coil region embedded within the coil structure, as in the above-described embodiments, the embodiments described with reference to FIGS. 7-19 have a tensile support member embedded within the coil structure, or have a passageway for the mounting of a tensile support member embedded within the coil structure.

FIG. 7 schematically shows a cross-section of a shield coil 128 according to an embodiment of the invention. The shield coil 128 comprises two regions 134 of coil windings, a tensile support member 110 and electrically insulating layers 112 which serve to electrically insulate coil windings in regions 134 from an electrically-conductive tensile support member 110. The tensile support member is typically of a metal. If the tensile support member 110 is of an electrically non-conductive material such as a glassfiber composite, the insulating layers 112 may not be necessary. Insulating layers 112 may comprise respective layers of glassfiber cloth which are resin impregnated in a single impregnation step with the coil windings.

Tensile support member 110 is preferably curved to suit the radius of curvature of the coil windings at the location that the tensile support member is positioned. In the illustrated embodiment, a section 114 of the tensile support member 110 embedded in the shield coil 128 and in the vicinity of the coil is curved, while a section 116 distant from the coil is planar. In addition, within the planar section 116, thinned parts may be provided as flexures 118 to accommodate relative radial movement resulting from differential thermal contraction during cooling of the magnet coil structure, and expansion of the shield coil due to mechanical forces on energization as well as thermal expansion resulting from a coil quench. Another desirable and intended feature of the chosen support system is that all degrees of freedom, both rotational and translational are well constrained with the exception of the radial degree of freedom which has sufficient compliance to allow the coil to move freely. In other embodiments, the tensile support member 110 may be planar along its entire length, or may be curved along its entire length, although flexures 118 may be inappropriate in such a curved embodiment but can still be easily incorporated if short planar sections are pressed into otherwise curved supports as shown in FIG. 9A. A mounting feature 120 is provided to the tensile support member 110. In the illustrated embodiment, the mounting feature may be a simple hole in the tensile support member for attachment to a clevis pin. Multiple tensile support members are provided, spaced around the circumference of the shield coil 128 in a number sufficient to provide appropriate mechanical retention and to control coil bending within required limits. Around the circumference of the shield coil 128, spacers 122 are provided to fill gaps between tensile support members 110 such that, at the radial location of the tensile support members 100, the spacers 122 and radial support members 110 alternate. If filled-resin systems are used, such as those incorporating aluminum oxide (e.g. Stycast), then the spacers may be deleted as any gaps will be filled with the filled-resin. The coil structure disclosed may be formed either by vacuum impregnation or by a wet-winding method. FIG. 8A shows a perspective view of a shield coil according to this embodiment of the invention. In this embodiment, six tensile support members 110 are provided, spaced around the circumference of the coil. Spacers 122 fill in gaps between the tensile support members 110. Arrow 126 illustrates the direction of an overall electromagnetic force acting on the coil when in use. Clearly, in use, the tensile support members 110 must resist this electromagnetic force. In addition, the tensile support members 110 must also support the gravitational force on the shield coil 128 at all times including loads resulting from magnet movement during shipping or rigging (installation) as well as possible seismic events after installation.

Figure 8B:
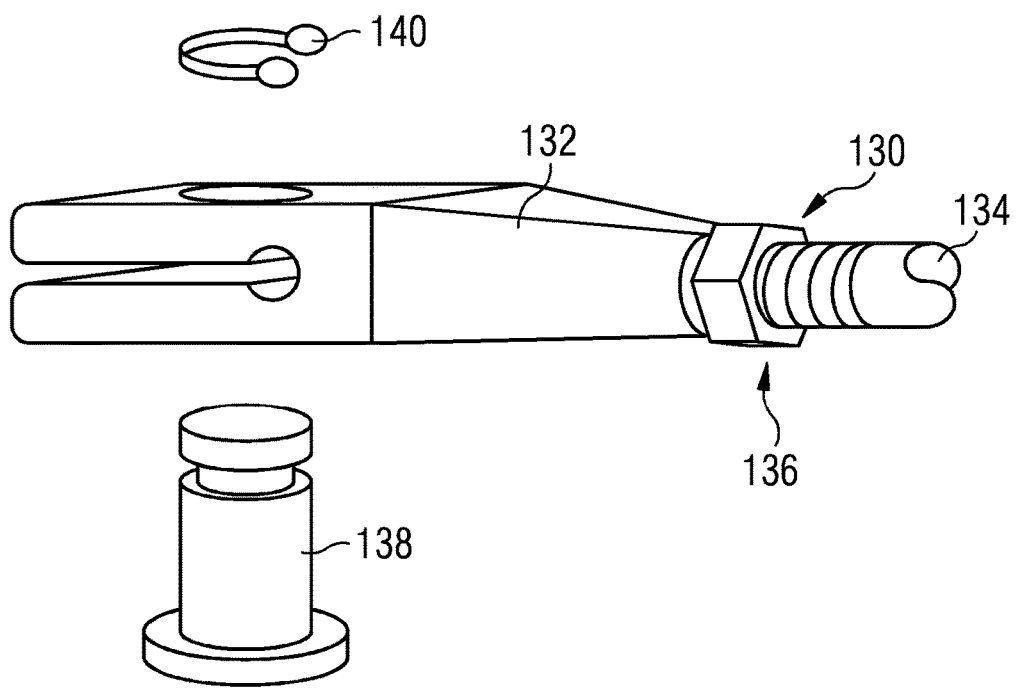
FIG. 8B shows a view of a suitable connector for interfacing the coil assembly shown in FIGS. 7 and 8A with the remainder of the magnet.
Figure 9A:
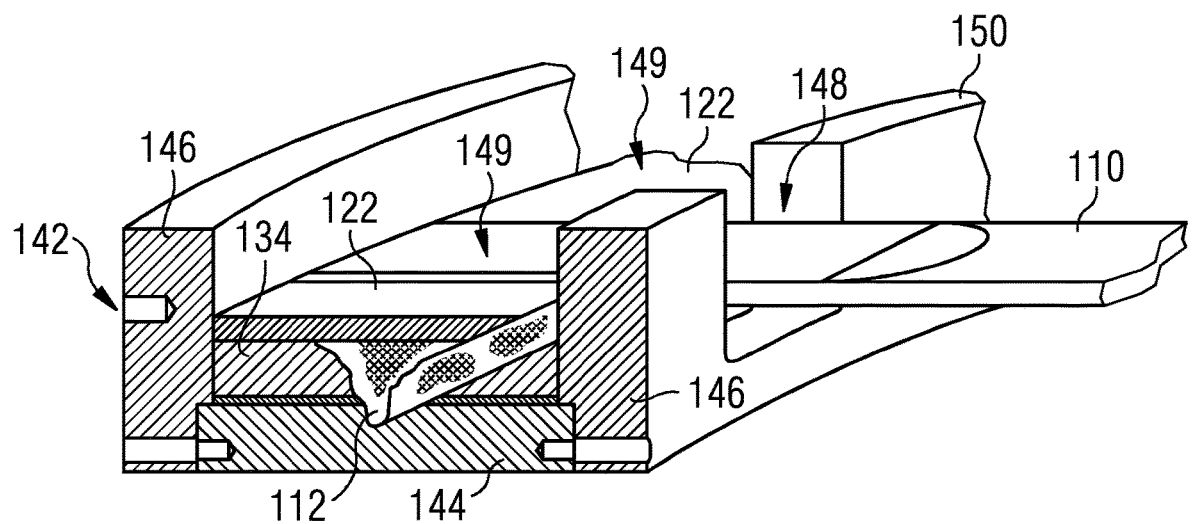
FIGS. 9A-9B show stages in a manufacturing process of a coil such as shown in FIGS. 7-8.

FIG. 8B shows a clevis arrangement 130 suitable for mounting the shield coil 128. Clevis arrangement 130 forms part of a shield coil mounting structure 26. Clevis arrangement 130 is conventional in itself, comprising clevis 132 retained on a rod 134 by an adjustable arrangement 136, in this case comprising a threaded end of rod 134 in a threaded hole within the clevis, and a locking nut; retaining pin 138 to fit into and traverse holes 120 in the tensile support member 110 and a retainer 140, in this case a circlip, for holding the retaining pin in place.

The clevis will act to retain a tensile support member 110 in tension against the electromagnetic force represented by arrow 126 and will support a tensile support member 110 in compression against the gravitational force on the shield coil 128. In a complete magnet coil assembly 10, a corresponding number of clevis arrangements 130 and tensile support members 110 should be provided. Corresponding structures may be provided at both shield coils 24. In some magnet coil assemblies, more or fewer than two shield coils 128 may be provided, in which case the mounting arrangement consisting of tensile support elements 110, clevis arrangement 130 and rod 134 may be adapted to suit. The adjustable elements incorporated into the clevis assemblies allow for easy and cost effective adjustment of the coil positions to optimize the magnetic field uniformity.

Figure 9B:
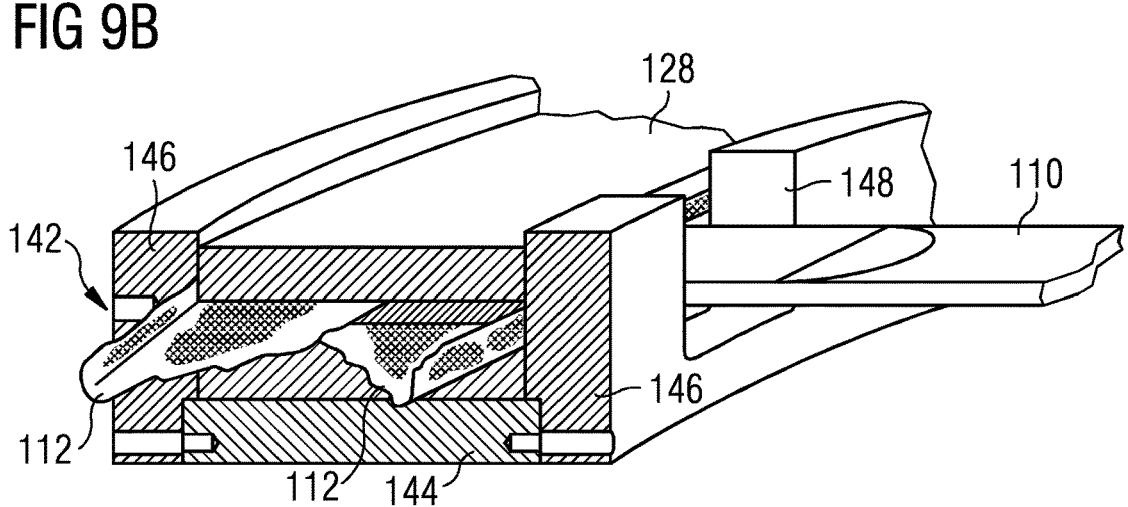

FIGS. 9A-9B schematically illustrate cross-sections of two stages in a process for manufacture of an end coil 128 such as illustrated in FIG. 8A. As is conventional, a demountable coil mold 142 is provided, comprising a cylindrical piece 144 and end pieces 146.

As illustrated in FIG. 9A and according to a feature of the method of the present invention, cutouts 148 are provided in circumferential locations corresponding to the required locations of tensile support members 110, and extending from a radially outer extremity 150 of an end piece 146, deep enough to extend over the required radial position of the tensile support members 110. As illustrated, a first volume 134 of coil windings is provided in the conventional manner, up to the required radial position of the tensile support members 110. An insulating layer 112 is then provided over the coil windings. This may be a glassfiber cloth layer. The coil windings and the insulating layer may be dry wound or wet wound, as in conventional arrangements. Next, tensile support members 110 are placed in position, over the insulating layer 112 at required locations and spacers 122 are positioned between the tensile support members to provide an approximately continuous surface 149.

A second insulating layer 112 is then placed over the tensile support members 110, and preferably also over spacers 122. A second volume 134 of coil windings is provided in the conventional manner, over second insulating layer 112 to complete the coil. FIG. 9B shows the end coil 128 in its mold at this stage. Where the coil and insulating layers have been wet wound, the resin is caused or permitted to harden. Preferably, a simple mechanical arrangement is provided to retain the tensile support members 110 in their respective fixed positions with respect to the coil mold. Where the coil and insulating layers have been dry wound, the wound assembly of coil windings, insulating layers 112, tensile support members 110 and spacers 122 must now be impregnated.

Figure 10:
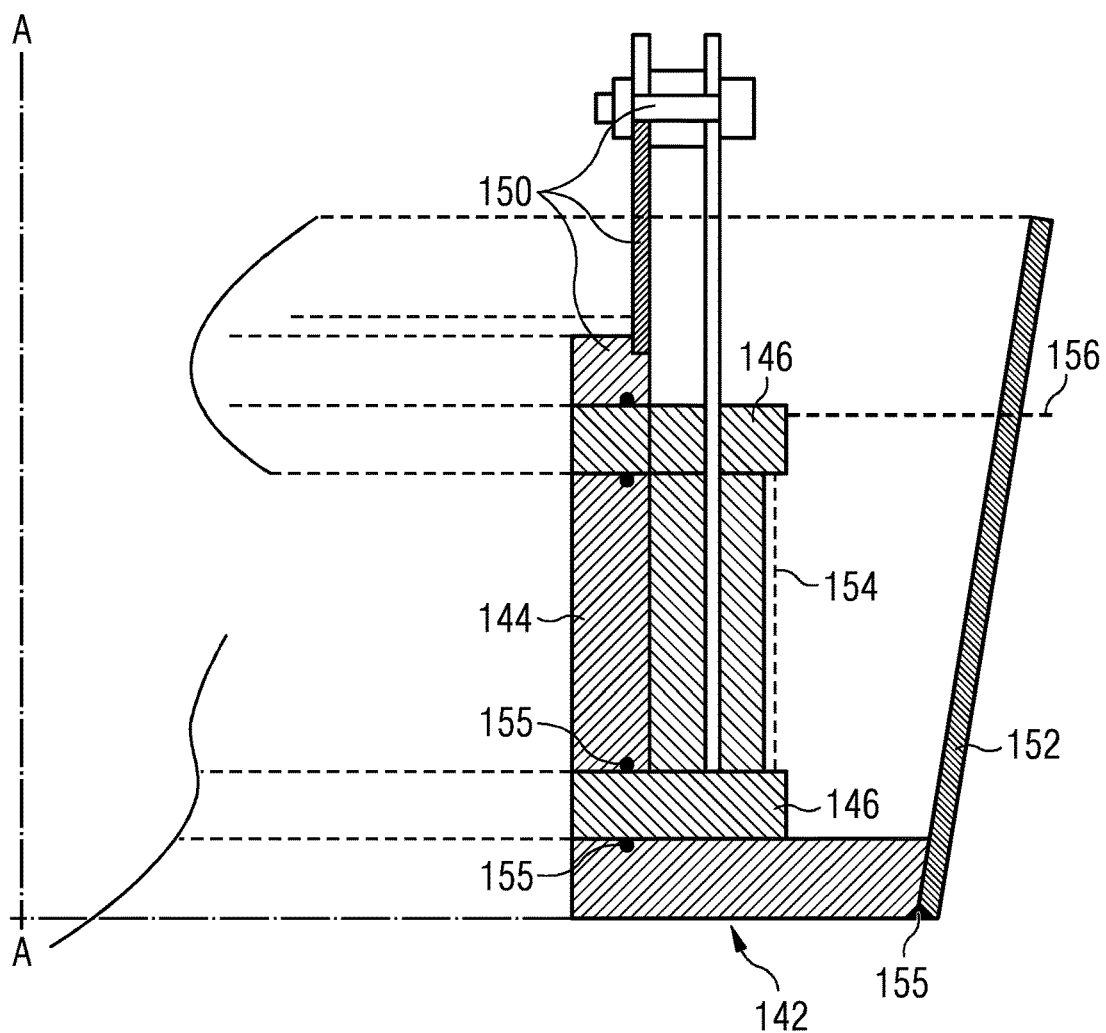
FIG. 10 shows a further stage in a manufacturing process of a coil such as shown in FIGS. 7-8.

FIG. 10 shows a schematic cross-section through an arrangement for impregnating the end coil 128 of the present invention. Mechanical support arrangements 150, which may be known as "jigging fixtures", are provided and attached to the mold 142, to retain the tensile support members 110 in the required positions with respect to the mold 142. Impregnation trough 152 is attached to mold 142, and a layer of release cloth 154 is provided over the radially outer surface of the coil. Seals 155 are provided, as is conventional in itself, to prevent leakage of resin from the trough.

As is conventional in itself, resin floods the resin trough, under vacuum, to a flood level 156. The resin is then caused or permitted to harden, and removed from the trough 152 when the resin has gelled, using the release cloth 154 to separate the radially outer surface of the coil from the bulk of resin.

Figure 11:
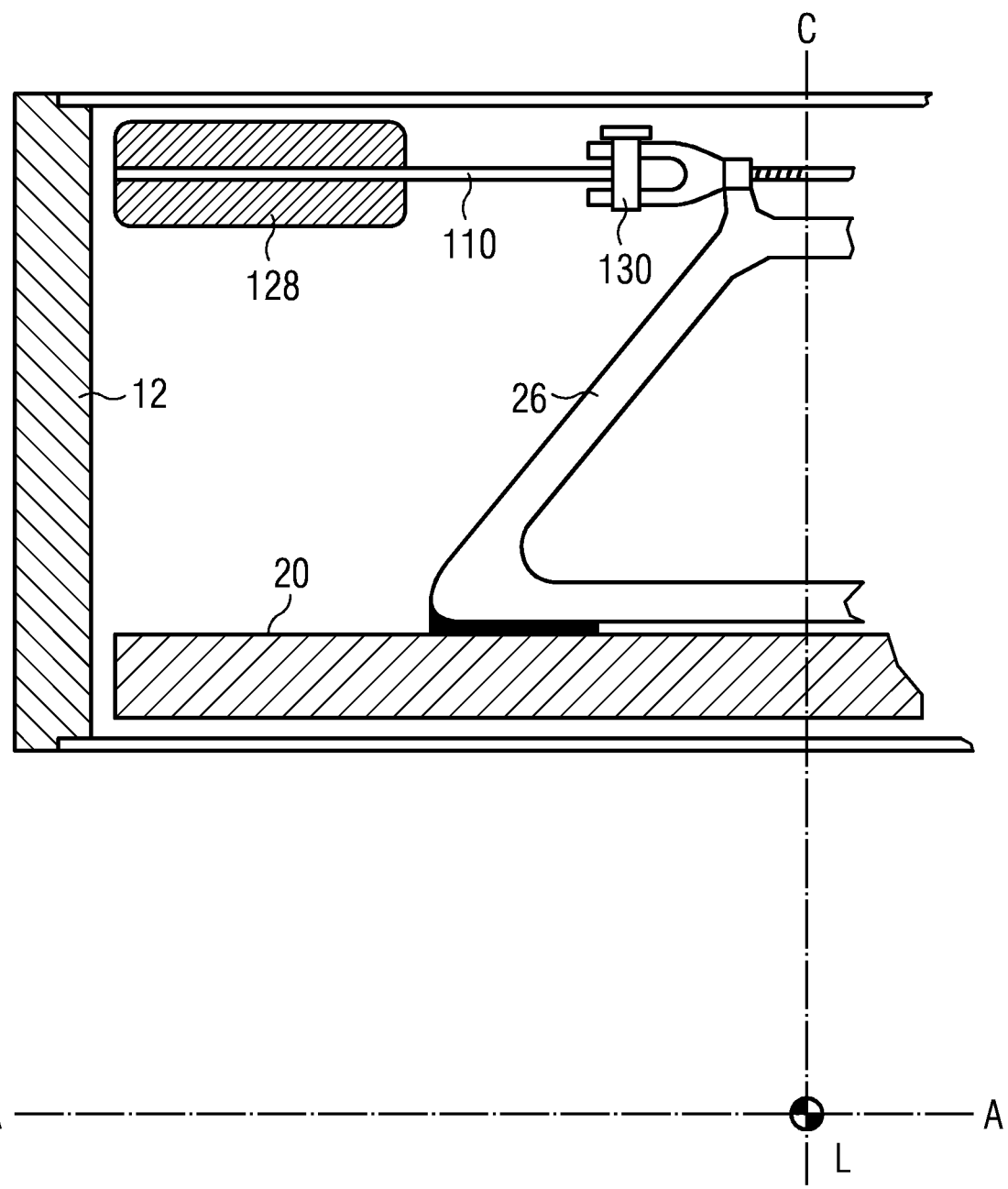
FIG. 11 shows a schematic partial axial cross-section through an actively-shielded superconducting magnet of the present invention.

FIG. 11 shows a more detailed partial cross section of a shield coil 128 of the present invention mounted in a cryogen vessel. Clevis arrangement 130 of FIG. 8 is mounted to the shield coil support structure 26. Shield coils 128 are supported and retained in position by tensile support members 110. As illustrated, as no former or journal is required to support the shield coils 128, they may be placed close to the axial and radial extremities of the cryogen vessel 12, in their most effective available position. This has the effect of minimizing usage of expensive superconducting wire as compared to equivalent coils in journals which cannot be located as close to the axial and radial extremities of the cryogen vessel 12; and/or the stray field of the magnet can be more effectively optimized within a given space envelope.

Conventional coil journals are expensive and heavy to manufacture and prevent the shield coils from being placed in their optimum position: near the axial and radial extremities of the cryogen vessel 12. In this optimum position, the number of turns in the shield coil may be reduced, reducing coil costs. The positioning of shield coils is not as critical as for coils of the inner magnet 20, so some tolerance in the mounting arrangement can be permitted.

Figure 12:
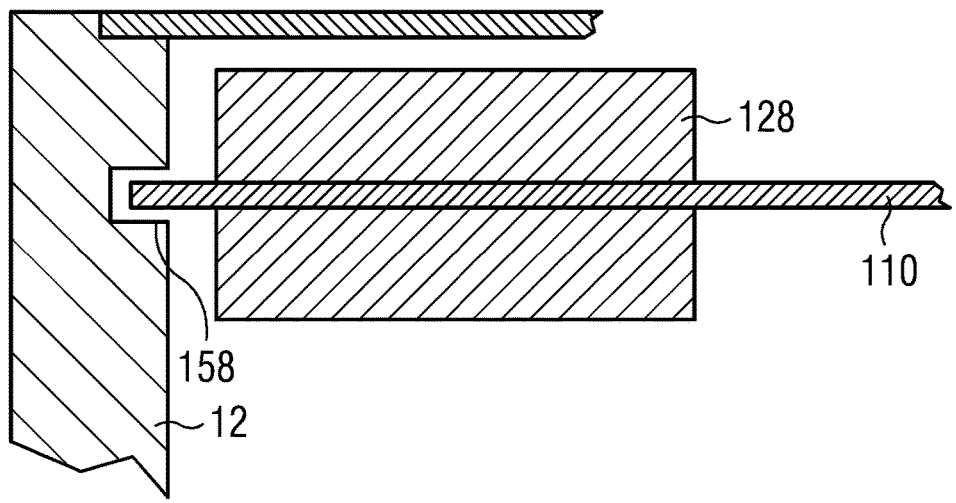
FIG. 12 shows a detail of the embodiment of FIG. 11.

FIG. 12 shows a detail of a mounting arrangement for a shield coil, according to another embodiment of the present invention. In this embodiment, the tensile support member 110 extends axially through the coil 128 and protrudes from the coil at its axially outer surface. This may be accommodated in the manufacturing process of FIGS. 9A-10 simply be providing similar cutouts 148 in both end pieces 146 of the mold 142.

As shown in FIG. 12, a recess 158 may be provided on the inner surface of the cryogen vessel to accommodate the protruding end of the tensile support member 110. Recess 158 is preferably not a tight fit to the protruding end of the tensile support member 110, but provides a limitation to its range of movement, providing axial and radial retention to end coils 128 during transit or during other high impact mechanical events. The protruding end of the tensile support member 110 and the recess 158 co-operate to provide a bump-stop arrangement to react against the ends of the cryogen vessel either directly (as shown) or via interfacing components as will be apparent to those skilled in the art.

Figure 13:
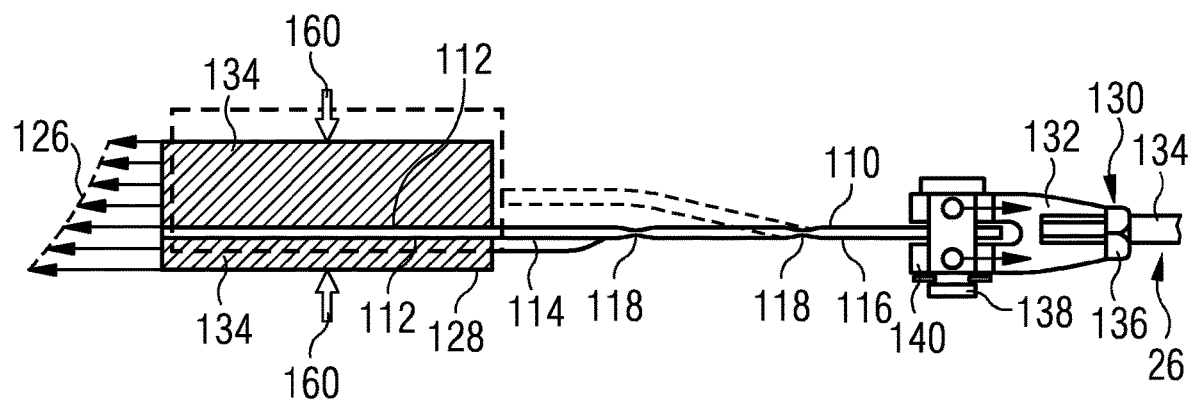
FIG. 13 shows a schematic part-axial cross section of a coil assembly according to an embodiment of the present invention.

FIG. 13 illustrates the relative movement of the shield coil 128 as compared to shield coil mounting structure 26 including clevis arrangement 130. Such relative motion may be due to differences in thermal expansion and contraction between shield coil 128 and shield coil mounting structure 26, or due to expansion of the shield coil 128 due to electromagnetic forces, sometimes known as "hoop forces". Additionally the coil will tend to expand during a quench event and this movement will also be effectively accommodated by the disclosed support system. The shield coil is shown in its "rest" position, and shown in phantom in an "expanded" position—although the "expanded" position may in fact be due to the contraction of the shield coil mounting structure 26 by more than the contraction of the shield coil 128. In the illustrated embodiment, the tensile support member 110 includes two flexures 118 in a planar section 116. In this embodiment, and preferably, no flexures 118 are provided in the curved section 114.

As illustrated, relative radial movement of the shield coil 128 and shield coil mounting structure 26 is accommodated by bending of the tensile support members 110 at the flexures 118. This does result in some axial displacement of the shield coils towards an axial mid-point of the magnet, but this displacement may be taken into account during the design stage of the magnet, and when shimming the magnet for magnetic field homogeneity in the imaging region.

In FIG. 13, arrows 160 illustrate electromagnetic forces acting radially on the shield coil 128. The combined effect may be a radial expansion, but the coil turns are also compressed radially, which helps to maintain the integrity of the bond between the shield coil 128 and the tensile support member 110. In particular, the radial forces 160 acting on the layers of turns of the shield coil 128 serve to compress the tensile support member 110, improving the durability of the bond between coil regions 134 and tensile support member 110.

The arrow 126 illustrating the axial force on the shield coil is divided up to represent relative axial force acting at differing radial positions on the shield coil 128. Radially inner turns tend to experience a greater axial force than radially outer turns. As illustrated, the position of the tensile support member 110 within the shield coil 128 may be displaced towards the axially inner surface of the shield coil 128 to reduce torque on the coil which may otherwise be caused by the varying distribution of axial forces on the windings of shield coil 128, in which direction the tensile support members 110 are stiff.

The tensile support members 110 are flexible in the radial direction but stiff in all other directions. They are stiff enough to support the weight of the coil 128 under gravity, but flexible enough to allow it to expand radially due to differential thermal expansion or contraction, or electromagnetic forces. Due to the flexibility of the tensile support members 110 in the radial direction, the weight of the coil 128 may largely be supported by tensile support members at the sides of the coil, where the coil weight is experienced as a transverse bending moment on the tensile support members 110.

The tensile support members 110 may be surface treated to provide effective adhesion of resin. For example, this may be by anodizing of aluminum tensile support members, sand blasting, knurling, abrasion or other surface texturing. Indentations or through-holes may be provided in the tensile support members to provide effective axial retention.

Figure 14:
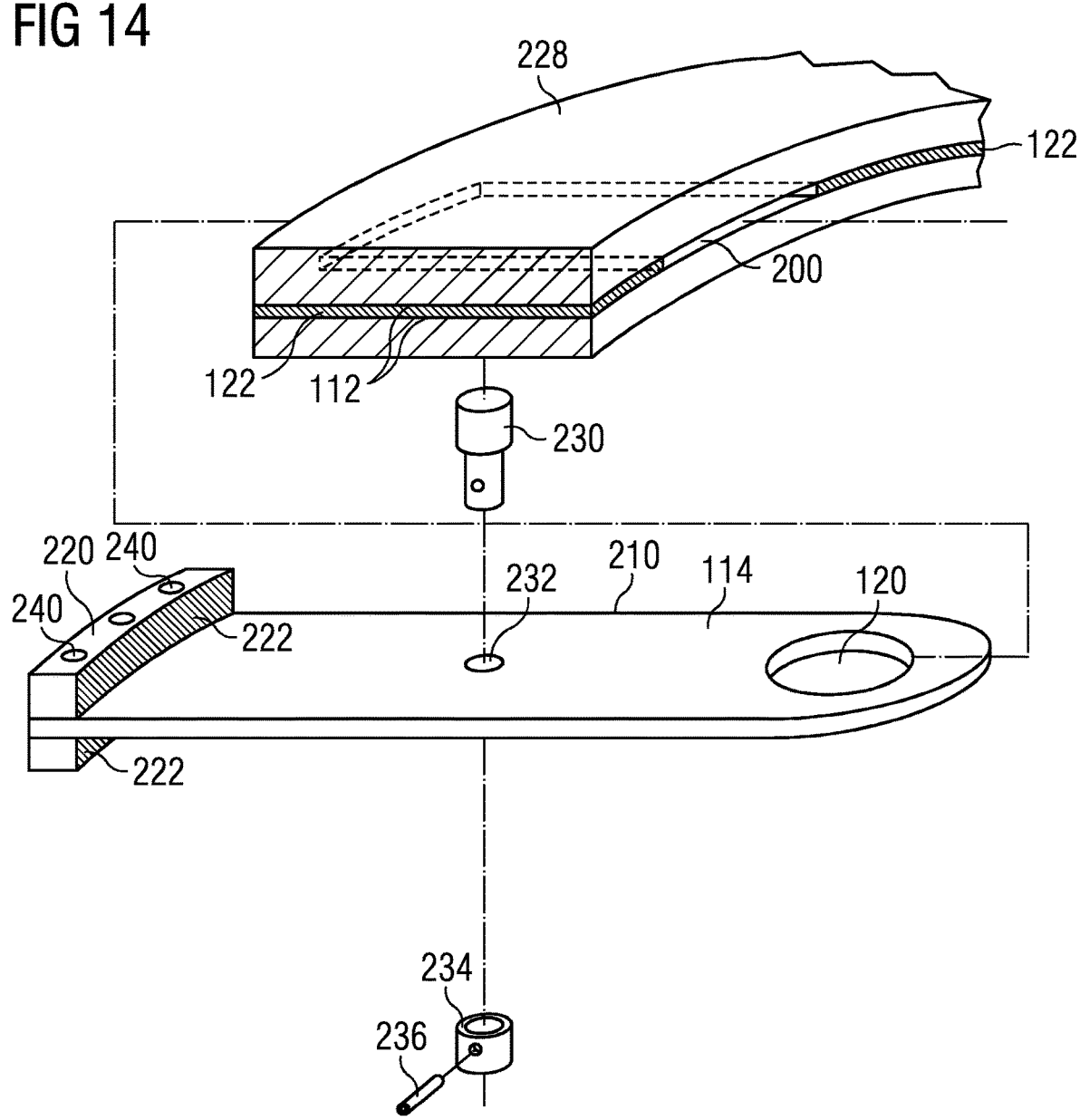
FIG. 14 shows a schematic section of a partially disassembled embodiment of the present invention.

FIG. 14 illustrates an example of another set of embodiments of the present invention. Here, instead of tensile support elements being bonded to the coil, passageways 200 are provided axially through the shield coil 228. Separate tensile support members 210 are provided, and are slid through the passageways to provide a mounting arrangement for shield coils 228. Spacers 122 and insulating layers 112 are provided, as for the embodiment of FIGS. 9A-9B.

Passageway 200 may be formed by embedding a removable piece in much the same way as the tensile support member 110 of FIGS. 9A-10 was embedded, then removing the removable piece once the resin has cured. The removable piece may be coated in a release agent to ensure that it does not become bonded to the resin. The passageway 200 may be curved to match the curvature of the coil windings. Alternatively, the tension elements and thrust blocks may be coated with a release material such as PTFE allowing them to be incorporated into the coil during manufacture. After the coil is complete and the resin cured, the elements will be free to slide in the coil. A further possibility is by including a spacer of relatively low melting point material, such as a wax, in the structure as wound, and melting it away once the impregnating resin has cured. Similarly, such a spacer may be provided, of a soluble material, which is dissolved by an appropriate solvent once the impregnating resin has cured.

The tensile support member 210 may be curved 114 along its entire length to match the curvature of the passageway 200, to enable it to pass through the passageway 200. A thrust block 220 is provided at the axially outer end of the tensile support member 210 to provide a retaining surface 222 for the shield coil 228. The thrust block 220 is preferably provided on both radially inner and radially outer surfaces of the tensile support member 210, and the retaining surface 222 should be provided with a low friction surface covering such as PTFE.

As indicated by the chain-line, in use, the tensile support member 210 is inserted through passageway 200 until the retaining surface 222 of thrust block 220 contacts the axially outer surface of the shield coil 128. The tensile support member 210 should not be a tight fit into the passageway 200, nor should it be so loose that it allows excessive movement. A hole 120 may be provided for attachment to a retaining structure, in the manner described above. As the tensile support member 210 is not bonded to the shield coil 128, a retainer should be provided to prevent the tensile support member 210 from falling out of the coil. This retainer may, as illustrated, be in the form of a coil retaining pin 230 passing through a hole 232 in the tensile support member 210 and held in place by a retaining sleeve 234 and a retaining pin 236. Thrust block 220 may comprise two blocks, held together by retaining pins 240.

Figure 15:
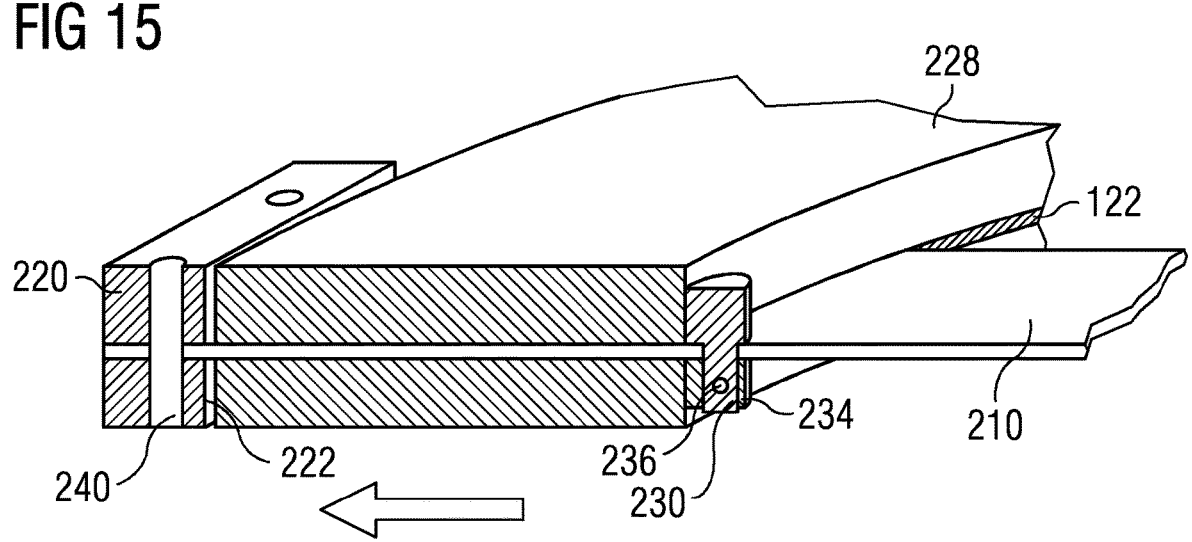
FIG. 15 shows a schematic section of the embodiment of FIG. 14 when assembled.

FIG. 15 shows a cross-section of the components of FIG. 14 assembled together. As the tensile support member 210 is not bonded to the coil structure, this arrangement may be found more suitable for arrangements in which the thermal contraction of the tensile support member 210 differs from the thermal contraction of the coil, or for shield coils subjected to high axial stress, since the coil will be under axial compression in this arrangement rather than axial tension.

Figure 16:
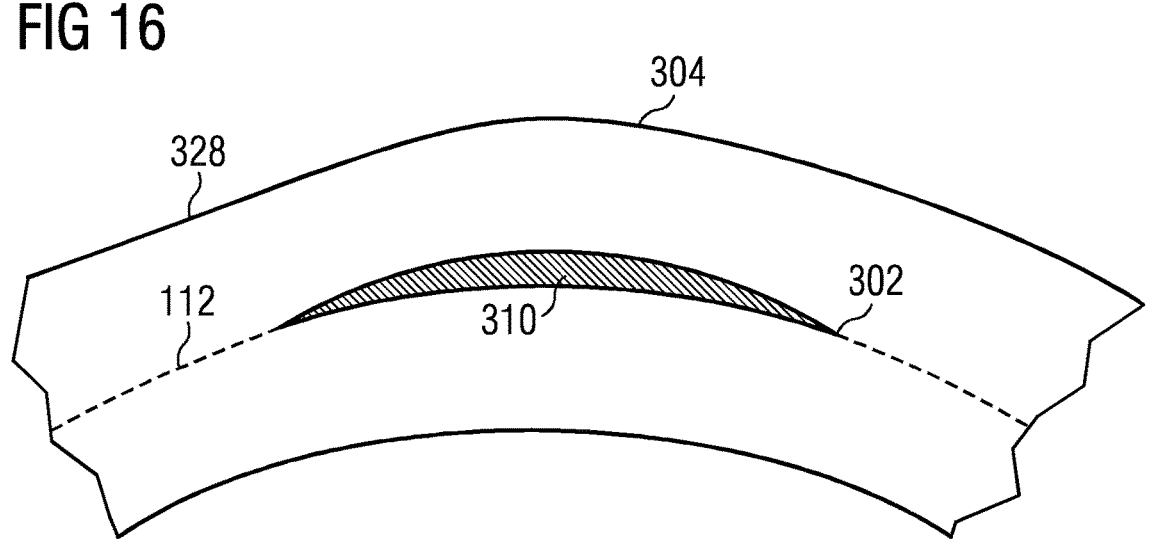
FIG. 16 shows a schematic partial radial cross-section of a coil according to a further embodiment of the present invention.

FIG. 16 shows a schematic part-radial cross-section of a coil 328 according to a variant of the present invention. In this variant, the tensile support member 310 is of shaped radial cross-section: essentially curved to suit the curvature of the coil windings, but tapered at its circumferential edges. Coil windings may be wound over such tensile support members yet leave only a small resin-filled volume 302 at each circumferential edge of the tensile support member. Depending on the material chosen for the tensile support members 310, insulating layers 112 may be provided. If a non-electrically conductive material, such as a glass-reinforced plastic (GRP) material, is chosen, then the insulating layers may be omitted. Surface treatment, which may include indentations, anodizing, texturing or through-holes, may be provided to the tensile support member 310 as described above. In such arrangement, the radially exterior surface of the coil is no longer annular, but includes deformations 304 at locations where the tensile support members 310 are placed. Such deformation is unlikely to be problematic in the case of shield coils, and in any case can be taken into account during modelling and shimming of the magnet for optimum homogeneity in the imaging region 21.

Figure 17:
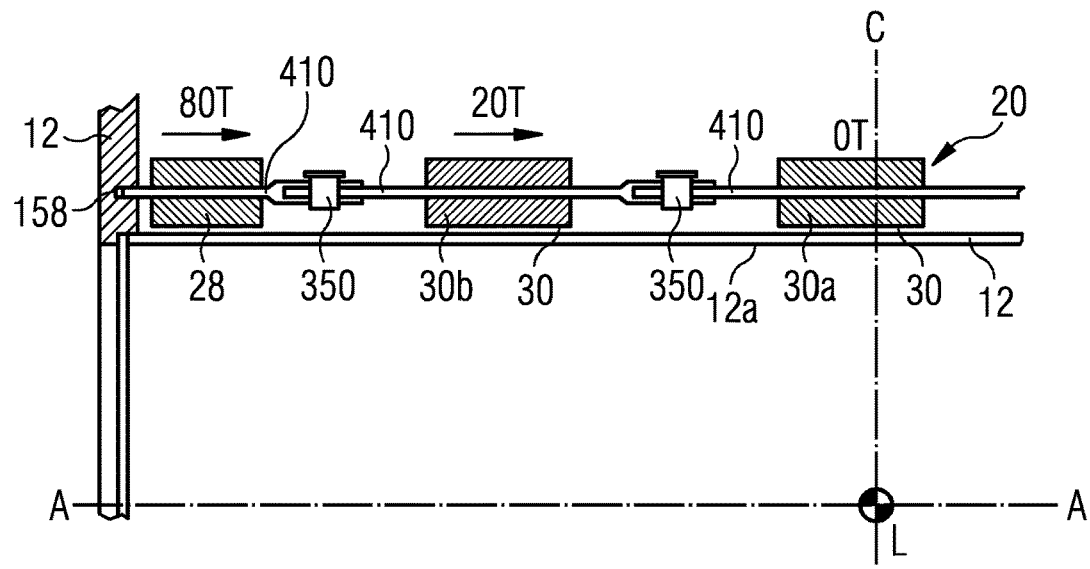
FIG. 17 shows a partial axial cross-section of a magnet assembly according to an embodiment of the present invention.

FIG. 17 shows another embodiment of the invention. In this embodiment, superconducting end coils 28 and inner coils 30 are provided with support members 410 according to an embodiment of the invention, to form an inner magnet structure 20 mounted within a cryogen vessel 12. Each of the coils 28, 30 is provided with a number of support members 410, each of which traverses the associated coil axially. Joints 350 join corresponding ones of the tensile support members to one another to construct the inner coil assembly. Each of the joints may comprise a clevis arrangement, or may be bolted or bonded together, or any other suitable arrangement as will be apparent to those skilled in the art. Typically, as will be apparent to those skilled in the art, the coils 28, 30 of the inner coil assembly 20 will be subjected to axially-inwardly directed forces caused by electromagnetic effects. A central inner coil 30a may be subjected to a zero net axial force, while an axially-outer inner coil 30b may be subjected to an axially inward force of some seventy tons, for example, and end coil 28 may be subjected to an axially inward force of some eighty tons, for example. In this embodiment, the support members 410 are in compression, and their structure and the structure of joints 350 must be suitable to withstand such compressive axial loads.

Mechanical support for the inner coil assembly is provided by an arrangement similar to that described with reference to FIG. 12. A support member 410 protrudes beyond the axial extremity of each of the end coils 28 and is received in a recess 158 formed in the corresponding inner surface of the cryogen vessel 12 to accommodate the protruding end of the support member 410. To prevent the inner magnet assembly 20 from moving, or from applying an axial tension to the cryogen vessel 12, it is preferred that at one axial end of the cryogen vessel, the corresponding protruding end of the support member 410 is attached to the cryogen vessel by a suitable method such as bonding, bolting, welding and so on, and at the other axial end, the protruding end of the support member 410 rests within the corresponding recess 158 but is able to move axially. This allows the inner magnet structure 20 to be supported by the support members 410 on the cryogen vessel 12. In alternative embodiments, the coils 28, 30 may rest on the bore tube 12a of the cryogen vessel 12, such that their weight is borne by the bore tube 12a, but the coils are held in alignment and axially retained by the support members 410.

The support members 410 should be curved over some, if not all, of their length, which provides additional mechanical strength, and resistance to buckling, in the axial direction. Each recess 158 in the cryogen vessel creates an end constraint for the associated support members 410. As the axially protruding end of the support member 410 may be relatively short, it may be mechanically strong, which in turn allows each end coil 28 to serve as a rigid end constraint for the next axially adjacent set of support members 410.

Towards the axial center-line C-L of the magnet structure, the axial forces on the relevant coils accumulate. In an example, an axial force of around eighty tons on the end coil 28 and an axial force of around fifteen tons on the inner coil 30b sum together such that a force of ninety-five tons must be borne by support members 410 linking central coil 30a and the adjacent inner coil 30b. In order to support this summed force, more support members 410 may be provided linking central coil 30a and the adjacent inner coil 30b than provided in axially-outer positions, such as linking end coil 28 with the adjacent inner coil 30b.

Figure 18:
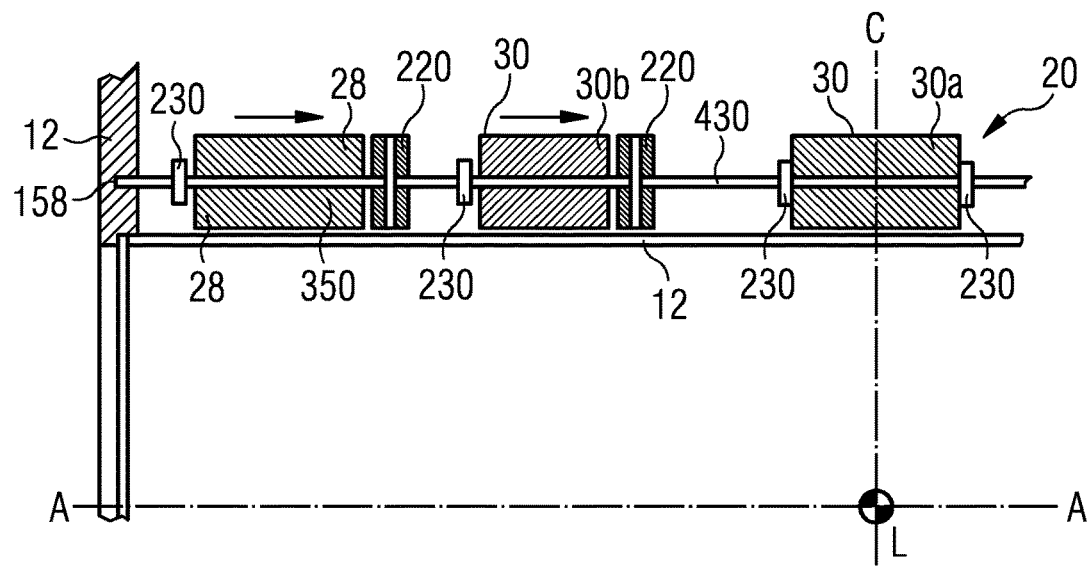
FIG. 18 shows a partial axial cross-section of a magnet assembly according to another embodiment of the present invention.

FIG. 18 shows another embodiment of an inner magnet assembly 20 of the present invention. This embodiment resembles the embodiment of FIGS. 14-15, wherein a support element passes through a passageway formed within the coil structure. The construction of the coils, the passageways and spacers is as described with reference to FIGS. 14-15, but a significant difference lies in the fact that coil support bars 430 extend through a plurality of coils. In the illustrated embodiment, each coil support bar 430 extends between both end walls of the cryogen vessel 12. Each coil support bar 430 may be welded or otherwise firmly attached to the cryogen vessel at both of its ends. In FIG. 17, the support elements are incorporated into the coils, such that it would be difficult to weld or otherwise attach the support elements to the cryogen vessel. Accurate location into the cryogen vessel is required, and desirable, which largely decouples the coils from the cryogen vessel and so avoids unwanted interactions. The support members 410 and coil support bars 430 may be either fixed or free to move within recesses 158. In the embodiment of FIG. 18, the coils are free to slide on the coil support bars 430, to some extent, so unwanted interactions between coils and cryogen vessel are avoided, even if the supports are rigidly fixed to the cryogen vessel. In certain embodiments, the coil support bars 430 may be rigidly attached at both ends to the cryogen vessel to also reinforce the cryogen vessel and withstand axial coil loads.

In each case, each coil support bar 430 is slid through multiple coils, 30a, 30b, 28 and retaining means are fitted as appropriate to hold the coils in the correct position on the coil support bars 430. In arrangements similar to that shown in FIGS. 14-15, thrust blocks 220 are provided to retain the coils against axial forces due to electromagnetic effects, while retainers such as retaining pins 230 with retaining sleeve 234 and retaining pin 236 are provided to retain the coils in position where electromagnetic loads do not need to be resisted. As the central coil 30a is not subject to any axial electromagnetic force, it need only be retained by retainers on both sides, and not be provided with any load-bearing thrust blocks. Of course, the coils may be provided with thrust blocks 220 even where not mechanically necessary and a retainer would have been sufficient. It may be possible to omit the retainers, relying on the axial forces on the coils when in operation to locate them in the correct positions adjacent their thrust blocks 220.

Figure 19:
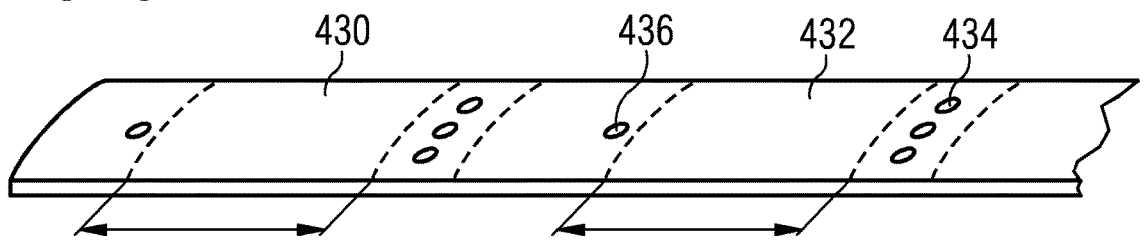
FIG. 19 shows a perspective view of a component of the embodiment shown in FIG. 18.

FIG. 19 shows an example of a coil support bar 430 which may be employed in an embodiment of the present invention as illustrated in FIG. 18. The coil support bar 430 is curved to match the curvature of the coil windings. Coil locations 432 are defined on the coil support bar and may be free from through-holes. The coil support bar 430 may be coated with a low-friction surface costing to avoid any stick-slip issue with coils suddenly moving, which might otherwise cause a quench. Sets of through-holes 434 may be provided in locations designated for thrust blocks 220, these holes being intended to allow retaining pins 240 to traverse the coil support bar 430 to retain thrust blocks. Further through-holes 436 may be provided for mounting of retainers.

During the assembly process, coils 28, 30 of the inner coil assembly 20 are aligned, and coil support bars 430 are passed through corresponding passageways 200 in the coils, and the coils and coil support bars 430 are fixed in their relative positions by installation of thrust blocks 220 and retainers.

The resulting inner magnet assembly is then installed into the cryogen vessel, preferably as the cryogen vessel is constructed, by welding or otherwise firmly attaching the coil support bar 430 to the end walls of the cryogen vessel.

This may be assisted by the provision of suitable recesses 158 in the end walls of the cryogen.

In embodiments such as shown in FIGS. 7-19, tensile support members 110, 210, 310, 410, 430 are preferably, and as illustrated, located between coil regions 34, 134 near a radial mid-point of the corresponding coil. In embodiments such as shown in FIGS. 7-13, 17, where the tensile support members are bonded to the coil volumes, radial compression forces illustrated in FIG. 13 compress the tensile support member, reducing the risk of delamination at the surface of the tensile support member. In an alternative structure, where a tensile support member could be bonded to a radial or axial extremity of the coil, a shear force would act on the interface of the tensile support member and may lead to delamination and failure of the bond between coil and tensile support member.

In all embodiments, it is preferred that the tensile support member and any passageway for the tensile support member should be located towards the radial mid-point of the corresponding coil. This is a relatively stable location from consideration of wire performance. An advantage of such positioning arises in that, should a failure arise, for example due to a crack forming in the impregnating resin at the interface with the coil support member or the passageway for the coil support member, risk of a resulting quench is reduced as compared to a crack forming at an interface near a radially inner or outer extremity of the coil, since the magnetic field strength near a radially inner or outer extremity of the coil is greater than the magnetic field strength towards the radial mid-point of the corresponding coil.

Accordingly, in embodiments such as shown in FIGS. 7-19, a strong interface with the tensile support members is provided, such that cracking or delamination of the bond is unlikely to occur, and the risk of resultant quench is reduced in case of such cracking due to the reduced magnetic field strength at the location of the tensile support members, being towards a radial mid-point of the corresponding coil.

The present invention accordingly provides several embodiments of coil mounting structures in which coil mounting arrangements include features embedded within the structure of the coil, adjacent to turns of the coil. Preferably, the features embedded within the structure of the resin-impregnated superconducting coil are located between layers of turns of the coil. In certain embodiments, the embedded features comprise non-coil regions which may be used to attach support elements. Such embodiments may be particularly useful in magnet systems where the support elements between coils are in compression, in use. In other embodiments, the embedded feature is a tensile support element, bonded into the structure of the coil between layers of turns. This embodiment may be particularly useful in embodiments where the coils are subjected to an axially-outward electromagnetic force, in use. An alternative to the embedded tensile support member has passageways embedded within the structure of the coil, these passageways being used to mount tensile support elements which are provided with thrust blocks to retain the coil in place. Such embodiments may also be particularly useful where the coils are subjected to an axially-outward electromagnetic force, in use. Variants of this embodiment have several coils mounted on shared coil support bars, provided with thrust blocks as appropriate to the design of the magnet structure. Magnet assemblies may be constructed from coils of various embodiments of the invention, as appropriate to their function. The tensile support elements are axially-directed in each case, and are preferably located between layers of turns in a resin-impregnated coil structure.

The invention claimed is:

1. A resin-impregnated superconducting coil structure, comprising:
   a resin-impregnated superconducting coil; and
   an axially-extending coil mounting arrangement that includes at least one feature embedded within the resin-impregnated superconducting coil such that the at least one embedded feature is adjacent to and between layers of turns of the resin-impregnated superconducting coil.

2. A resin-impregnated superconducting coil structure according to claim 1, provided with axially-directed support elements mechanically linked to the resin-impregnated superconducting coil by an axially-extending structure embedded within the resin-impregnated superconducting coil.

3. A resin-impregnated superconducting coil structure according to claim 1, wherein the resin-impregnated superconducting coil comprises regions of coil windings and non-coil regions, forming the axially-extending structure and comprising an electrically insulating filler material, the electrically insulating filler material and the coil windings being resin impregnated in a single resin impregnation, into a single, monolithic structure, and wherein the axially-directed support elements are mounted to the non-coil regions.

4. A resin-impregnated superconducting coil structure according to claim 3, wherein at least one of the non-coil regions is annular and extends around the circumference of the resin-impregnated superconducting coil.

5. A resin-impregnated superconducting coil structure according to claim 3, comprising non-coil regions that extend radially through the coil, said non-coil regions comprising an electrically insulating filler material, the electrically insulating filler material and the coil windings being resin impregnated in a single resin impregnation, into a single, monolithic structure.

6. A resin-impregnated superconducting coil structure according to claim 3, comprising an ancillary component attached to a non-coil region.

7. A resin-impregnated superconducting coil structure according to claim 1, comprising an axially-directed tensile support member partially embedded within the resin-impregnated coil, located between layers of turns of the coil in the resin-impregnated coil structure.

8. A resin-impregnated superconducting coil structure according to claim 7 wherein a mounting feature is provided to the tensile support member.

9. A resin-impregnated superconducting coil structure according to claim 8, comprising multiple tensile support members spaced around the circumference of the resin-impregnated superconducting coil and embedded axially within the coil structure and each provided with a mounting feature.

10. A resin-impregnated superconducting coil structure according to claim 9, further comprising spacers circumferentially between tensile support members such that, at the radial location of the tensile support members, the spacers and tensile support members alternate.

11. A resin-impregnated superconducting coil structure according to claim 7 wherein, in use, radial forces acting on the layers of turns serve to compress the tensile support member between the layers of turns.

12. A resin-impregnated superconducting coil structure according to claim 11, further comprising a tensile support member provided with a thrust block, the tensile support member being inserted through passageway such that a retaining surface of the thrust block makes contact with an axial end-surface of the resin-impregnated superconducting coil.

13. A resin-impregnated superconducting coil structure according to claim 12, wherein the thrust block is provided on both radially inner and radially outer surfaces of the tensile support member.

14. A resin-impregnated superconducting coil structure according to claim 7 mounted to a support structure by a number of clevis arrangements, each retaining a corresponding tensile support member by a mounting feature, being a through-hole, through the material of the tensile support member.

15. A resin-impregnated superconducting coil structure according to claim 7 mounted within a cryogen vessel, wherein the tensile support member extends axially beyond the extent of the coil into a recess formed in a wall of the cryogen vessel, and the coil is supported against gravity by mechanical interaction between the recess formed in the wall of the cryogen vessel and the tensile support member.

16. A resin-impregnated superconducting coil structure according to claim 7 wherein the tensile support member is electrically conductive and the coil further comprises electrically insulating layers that electrically insulate the coil windings from the tensile support member.

17. A resin-impregnated superconducting coil structure according to claim 7 wherein the tensile support member comprises a section embedded in the resin-impregnated superconducting coil and in the vicinity of the coil is of curved cross-section, and a section distant from the coil that is planar.

18. A resin-impregnated superconducting coil structure according to claim 17, wherein thinned parts are provided as flexures within the planar section of the tensile support member.

19. An assembly of axially-aligned resin-impregnated superconducting coil structures each according to claim 7, wherein corresponding tensile support members of adjacent resin-impregnated superconducting coils are mechanically joined together.

20. An assembly of axially-aligned resin-impregnated superconducting coil structures according to claim 19, mounted within a cryogen vessel, wherein an end coil comprises tensile support members which protrude axially beyond an axial end-surface of the end coil into a recess formed in a wall of the cryogen vessel.

21. An assembly of axially-aligned resin-impregnated superconducting coil structures according to claim 19, mounted within a cryogen vessel, wherein an end coil comprises tensile support members which protrude axially beyond an axial end-surface of the end coil and wherein a protruding end of a tensile support member is attached to the cryogen vessel.

22. A resin-impregnated superconducting coil structure according to claim 1, comprising an axially-directed passageway embedded within the resin-impregnated coil, located between layers of turns in the resin-impregnated coil structure.

23. A resin-impregnated superconducting coil structure according to claim 1, wherein the resin-impregnated superconducting coil is from among an assembly of axially-aligned resin-impregnated superconducting coils, each comprising axially-extending coil mounting arrangements that include at least one feature embedded within the structure of a respective resin-impregnated superconducting coil, adjacent to turns of the coil, and wherein the assembly of the axially-aligned resin-impregnated superconducting coils comprises an end coil and an inner coil, the end coil comprising non-coil regions at one axial end thereof, the inner coil comprising non-coil regions at both axial ends thereof, and at least one support element joined between the end coil and the inner coil, mounted to the non-coil regions.

24. A resin-impregnated superconducting coil structure according to claim 23, comprising multiple separate support elements arranged around a circumference of the end coil and the inner coil.

25. A resin-impregnated superconducting coil structure according to claim 23, wherein the at least one support element is machined to provide an axial dimension.

* * * * *